(12) United States Patent
Volentine

(10) Patent No.: US 7,130,950 B1
(45) Date of Patent: Oct. 31, 2006

(54) PROVIDING ACCESS TO MEMORY CONFIGURATION INFORMATION IN A COMPUTER

(75) Inventor: Robert J. Volentine, Houston, TX (US)

(73) Assignee: Hewlett-Packard Development Company, LP., Houston, TX (US)

( * ) Notice: Subject to any disclaimer, the term of this patent is extended or adjusted under 35 U.S.C. 154(b) by 236 days.

(21) Appl. No.: 10/837,335

(22) Filed: Apr. 30, 2004

(51) Int. Cl.
*G06F 13/24* (2006.01)
*G06F 12/00* (2006.01)

(52) U.S. Cl. ................ 710/260; 710/261; 711/200
(58) Field of Classification Search ............ 710/260, 710/261; 711/200
See application file for complete search history.

(56) References Cited

U.S. PATENT DOCUMENTS

| | | | | |
|---|---|---|---|---|
| 4,744,048 A | * | 5/1988 | Blanset et al. | 715/806 |
| 6,154,825 A | * | 11/2000 | Murdoch et al. | 711/211 |
| 6,216,183 B1 | * | 4/2001 | Rawlins | 710/100 |
| 6,526,464 B1 | * | 2/2003 | Jobs et al. | 710/300 |
| 2005/0068831 A1 | * | 3/2005 | Johnson | 365/222 |
| 2005/0238359 A1 | * | 10/2005 | Dybsetter et al. | 398/135 |

OTHER PUBLICATIONS

Intel® 865G/865GV Chipset Datasheet—Intel® 82865G/82865GV Graphics and Memory Controller Hub (GMCH); Sections 3.9-3.10, pp. 1, 127-138; Feb. 2004.*

* cited by examiner

*Primary Examiner*—Rehana Perveen
*Assistant Examiner*—Jeremy S. Cerullo
(74) *Attorney, Agent, or Firm*—Kevin M. Hart

(57) ABSTRACT

Client software stores an identifier corresponding to memory configuration data of interest and causes a software interrupt that requests a memory configuration read function. An interrupt read function handler then reads the data of interest responsive to the identifier and returns the data of interest. The client software may include, for example, BIOS firmware or application software executing in real or protected mode. The memory configuration information may be stored in a hidden I/O or MMIO register device. In such an embodiment, the interrupt handler may enable access to the hidden I/O or MMIO register device prior to reading the data of interest and disable access to the hidden I/O or MMIO register device afterwards.

34 Claims, 1 Drawing Sheet

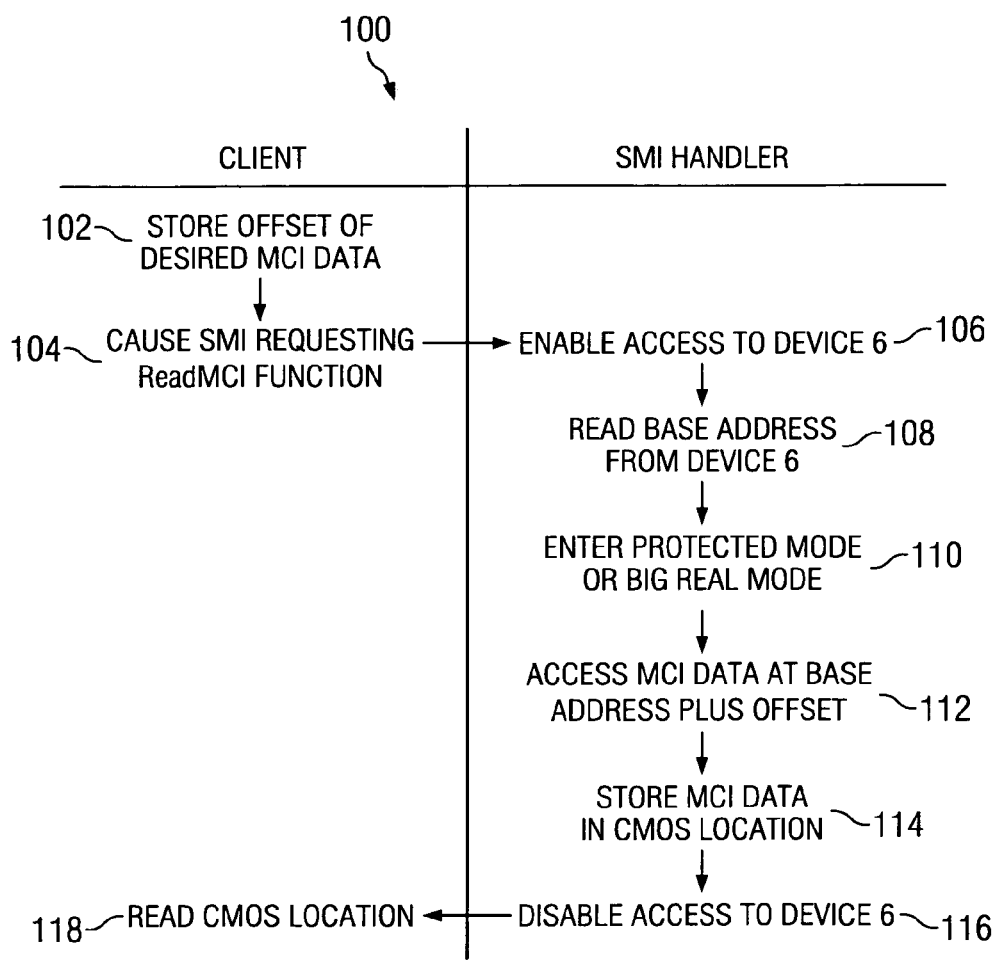

PROVIDING ACCESS TO MEMORY CONFIGURATION INFORMATION IN A COMPUTER

FIELD OF THE INVENTION

This invention relates generally to techniques for accessing memory configuration information in a computer.

BACKGROUND

The term "memory configuration information" ("MCI") refers generally to operational aspects of the dynamic random access memory ("DRAM") and related devices that are installed in a computer to provide the main memory resource of the computer. Such aspects could include, for example, the amount of memory installed, page sizes allowed during memory accesses, timing constraints to be observed when operating the DRAM devices, and other information.

A variety of systems executing on the computer may need to access memory configuration information at various times. For example, application software may need to access memory configuration information to make it available to a user during troubleshooting or testing of the computer. And basic input/output services ("BIOS") firmware, after setting the memory configuration information early in the boot process, may need to access the information later in the boot process.

Typically, memory configuration information is stored in one of the integrated circuit chips that comprise the "chipset" on the computer's motherboard.

SUMMARY OF THE INVENTION

In a method of accessing memory configuration information according to a preferred embodiment of the invention, client software stores an identifier corresponding to memory configuration data of interest and causes a software interrupt that requests a memory configuration read function. A software interrupt read function handler then reads the data of interest responsive to the identifier and returns the data of interest. The client software may include, for example, BIOS firmware or application software executing in real or protected mode.

In one embodiment, the memory configuration information may be stored in a hidden I/O or memory-mapped I/O ("MMIO") register device. In such an embodiment, the software interrupt handler may enable access to the hidden I/O or MMIO register device prior to reading the data of interest and disable access to the hidden I/O or MMIO register device after reading the data of interest.

BRIEF DESCRIPTION OF THE DRAWINGS

FIG. 1 is a flow diagram illustrating a method of accessing memory configuration information in a computer according to a preferred embodiment of the invention.

DETAILED DESCRIPTION OF THE PREFERRED EMBODIMENTS

Referring now to FIG. 1, a method 100 of accessing memory configuration information in a computer will now be described. In step 102, client software executing on the computer stores an identifier corresponding to memory configuration data of interest. The client software may be any process or thread executing on the computer—for example, the client may be BIOS firmware or application software executing in any mode including real or protected mode. The identifier may comprise any information that uniquely identifies the data. In a preferred embodiment, the identifier may comprise an offset from a base address at which a block of memory configuration information begins.

In step 104, client software causes a software interrupt. In response to the interrupt, an interrupt handler will read the data of interest corresponding to the stored identifier and will return the data of interest to the client software. In a preferred embodiment of the invention, the particular type of software interrupt caused is a system management interrupt ("SMI"). Although an ordinary software interrupt may be used to implement the invention, use of an SMI yields efficiency because an SMI automatically saves a substantial portion of the processor state when invoked, executes in a system management mode, and then automatically restores the saved state upon returning.

When causing the software interrupt or SMI, the client software specifies a read memory configuration information function to be invoked by an interrupt handler. In the illustrated embodiment, the client software performs this step by requesting a Read MCI function. The requested function may be specified by several means. In one preferred embodiment, the Read MCI function may be specified by writing a code in a CPU register prior to causing the interrupt. In another preferred embodiment, the Read MCI function may be specified by writing a code to a CMOS memory location prior to causing the interrupt. For example, the client may store a Read MCI function code in CMOS location 53 using I/O port 70 prior to causing the interrupt. In similar fashion, the identifier corresponding to the desired MCI data may also be placed either in a CMOS location or in a CPU register such as the SI register prior to causing the interrupt.

In some implementations, the memory configuration data of interest may be stored in a hidden I/O or MMIO register device. ("Hidden" when used herein with reference to a device is intended to mean the device is not normally accessible to software.) In such implementations, the process of reading and returning the requested data may include enabling access to the hidden I/O or MMIO register device prior to reading the data of interest and then disabling access to the I/O or MMIO register device after reading the data of interest. The flow diagram of FIG. 1 illustrates by way of example how this may be done in computers that are built using an Intel Corporation 865-series chipset. In such computers, the memory configuration information is stored a graphics and memory controller hub ("GMCH") chip of the chipset. Specifically, several PCI devices (devices 0–3 and 6) are implemented within the GMCH chip, and the memory configuration information is stored in numerous MMIO registers of device 6.

In step 106, the interrupt handler enables memory and I/O access to device 6. This may be done by setting bit 1 of the register at offset F4h in device 0 to enable access to device 6, and then by setting appropriate bits in registers of device 6 to enable memory and I/O accesses to device 6. In step 108, the interrupt handler reads the value stored in the base address register of device 6. This value corresponds to the base address for the MMIO registers containing memory configuration information. In step 110, the interrupt handler switches to the protected mode or the big real mode of the machine so that memory locations above 1 GB may be accessed. (This may also require loading a 4 GB selector in the CPU's DS register to allow data accesses anywhere within the 4 GB region.) In step 112, the interrupt handler accesses the memory configuration information corresponding to the identifier. This may be done, for example, by treating the identifier as an offset and reading the data beginning at the base address plus the offset.

In step 114, the interrupt handler returns the data to the client. This may be done using any of several techniques. For example, the return data may be placed in a memory location, in a CPU register, or in a CMOS location accessible by the client using an I/O cycle. In one preferred embodiment, only one byte of memory configuration information is read and returned in a single interrupt cycle. In other embodiments, more than one byte of memory configuration information may be read and returned in a single interrupt cycle. In step 116, the interrupt handler hides device 6 once again. This may be accomplished by writing to the memory and I/O access bits of device 6, and then by resetting bit 1 of the register at offset F4h in device 0 to disable access to device 6 altogether.

In step 118, the client reads the memory configuration information returned by the interrupt handler. In the illustrated embodiment, this may be accomplished by the client using an I/O cycle to read a specific CMOS memory location containing the return value. For example, the interrupt handler may place the return data in the CMOS location 54, and the client may read CMOS location 54 using an I/O port such as I/O port 71.

While the invention has been described in detail with reference to preferred embodiments thereof, the described embodiments have been presented by way of example and not by way of limitation. It will be understood by those skilled in the art that various changes may be made in the form and details of the described embodiments without deviating from the spirit and scope of the invention as defined by the appended claims.

The invention as described and claimed provides numerous advantages over the prior art. For the first time, application software executing in any mode including real or protected mode may access memory configuration information that is normally accessible only to processes or threads executing in protected or big real mode. Moreover, because this functionality is provided in the form of a software interrupt or a system management interrupt function, the functionality may be invoked efficiently by application software or BIOS firmware: The interface is simple, and complexity is hidden. Application programmers need not include code directly in their application software for providing this function. Rather, the requisite Read MCI function may be implemented within the BIOS firmware itself. Thus, code duplication is avoided and precious ROM space preserved. (The BIOS firmware may call itself at the Read MCI function entry point whenever this functionality is needed.) In addition, the invention provides a safe means for accessing memory configuration information: An I/O or MMIO register device containing the information is rendered inaccessible to client software both before and after the interrupt handler executes. Consequently, embodiments of the invention keep the memory configuration information safe from inadvertent accesses by unauthorized or erroneous software. Finally, the invention modularizes the task of accessing memory configuration information so that application software and client portions of BIOS firmware need not be changed with every change in chipset design.

What is claimed is:

1. A method of accessing memory configuration information in a computer, comprising:
    storing an identifier corresponding to memory configuration data of interest, the data of interest being stored in a graphics and memory controller hub ("GMCH") chip of an Intel 865 series chip set;
    causing a software interrupt that requests a memory configuration read function;
    in a software interrupt read function handler:
        enabling access to device 6 in the GMCH chip;
        reading a base address from device 6;
        entering a protected mode or a big real mode of the computer; and
        accessing the data of interest at an address corresponding to the base address plus the identifier; and
        returning the data of interest.

2. The method of claim 1, further comprising:
    disabling access to device 6 in the GMCH chip after accessing the data of interest.

3. The method of claim 1, wherein the data of interest is one byte in length.

4. The method of claim 1, wherein returning the data of interest comprises:
    storing the data of interest in a CMOS location accessible using I/o cycles of the computer.

5. The method of claim 4, wherein the CMOS location is location 54 and is accessible by a client using I/O port 71.

6. The method of claim 1, wherein returning the data of interest comprises:
    storing the data of interest in a CPU register.

7. The method of claim 1, wherein returning the data of interest comprises:
    storing the data of interest in main memory.

8. The method of claim 1, wherein the memory configuration read function is requested by storing a code in a CMOS location.

9. The method of claim 8, wherein the CMOS location is location 53 and is accessible by a client using I/O port 70.

10. The method of claim 1, wherein the memory configuration read function is requested by storing a code in a CPU register.

11. The method of claim 1, wherein storing the identifier and causing the software interrupt are performed by BIOS firmware executing in the computer.

12. The method of claim 1, wherein storing the identifier and causing the software interrupt are performed by application software executing in the computer.

13. The method of claim 12, wherein the application software is executing in the protected mode.

14. The method of claim 13, wherein the interrupt handler is executing in a protected mode or a big real mode of the computer.

15. The method of claim 12, wherein the application software is executing in a real mode of the computer.

16. The method of claim 15, wherein the interrupt handler is executing in a protected mode or a big real mode of the computer.

17. The method of claim 1, wherein:
    the software interrupt is a system management interrupt; and
    the software interrupt read function handler is a system management interrupt read function handler.

18. Storage media containing program code operable to cause a computer to perform a method of accessing memory configuration information, the method comprising:
    storing an identifier corresponding to memory configuration data of interest, the data of interest being stored in a graphics and memory controller hub ("GMCH") chip of an Intel 865 series chip set;
    causing a software interrupt that requests a memory configuration read function;

in a software interrupt read function handler:
   enabling access to device 6 in the GMCH chip;
   reading a base address from device 6;
   entering a protected mode or a big real mode of the computer; and
   accessing the data of interest at an address corresponding to the base address plus the identifier; and
   returning the data of interest.

19. The storage media of claim 18, wherein the method further comprises:
   disabling access to device 6 in the GMCH chip after accessing the data of interest.

20. The storage media of claim 18, wherein the data of interest is one byte in length.

21. The storage media of claim 18, wherein returning the data of interest comprises:
   storing the data of interest in a CMOS location accessible using I/O cycles of the computer.

22. The storage media of claim 21, wherein the CMOS location is location 54 and is accessible by a client using I/O port 71.

23. The storage media of claim 18, wherein returning the data of interest comprises:
   storing the data of interest in a CPU register.

24. The storage media of claim 18, wherein returning the data of interest comprises:
   storing the data of interest in main memory.

25. The storage media of claim 18, wherein the memory configuration read function is requested by storing a code in a CMOS location.

26. The storage media of claim 25, wherein the CMOS location is location 53 and is accessible by a client using I/O port 70.

27. The storage media of claim 18, wherein the memory configuration read function is requested by storing a code in a CPU register.

28. The storage media of claim 18, wherein storing the identifier and causing the software interrupt are performed by BIOS firmware executing in the computer.

29. The storage media of claim 18, wherein storing the identifier and causing the software interrupt are performed by application software executing in the computer.

30. The storage media of claim 29, wherein the application software is executing in the protected mode.

31. The storage media of claim 30, wherein the interrupt handler is executing in a protected mode or a big real mode of the computer.

32. The storage media of claim 29, wherein the application software is executing in a real mode of the computer.

33. The storage media of claim 32, wherein the interrupt handler is executing in a protected mode or a big real mode of the computer.

34. The storage media of claim 18, wherein:
   the software interrupt is a system management interrupt; and
   the software interrupt read function handler is a system management interrupt read function handler.

* * * * *